(12) United States Patent
Podhajsky et al.

(10) Patent No.: US 8,226,639 B2
(45) Date of Patent: Jul. 24, 2012

(54) SYSTEM AND METHOD FOR OUTPUT CONTROL OF ELECTROSURGICAL GENERATOR

(75) Inventors: Ronald J. Podhajsky, Boulder, CO (US); Kristin D. Johnson, Louisville, CO (US); Jason Case, Longmont, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 892 days.

(21) Appl. No.: 12/136,620

(22) Filed: Jun. 10, 2008

(65) Prior Publication Data

US 2009/0306648 A1    Dec. 10, 2009

(51) Int. Cl.
*A61B 18/12* (2006.01)
(52) U.S. Cl. .................................................. 606/34
(58) Field of Classification Search ............... 606/34
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |

(Continued)

FOREIGN PATENT DOCUMENTS

DE        179607        3/1905

(Continued)

OTHER PUBLICATIONS

Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

(Continued)

*Primary Examiner* — Michael Peffley
*Assistant Examiner* — Daniel Fowler (57) ABSTRACT

An electrosurgical system and method are disclosed. The system includes an electrosurgical generator adapted to supply electrosurgical energy to tissue. The generator includes sensor circuitry adapted to continuously monitor tissue impedance to generate a variance impedance curve and a microprocessor adapted to calculate a slope of a segment of the variance impedance curve. The microprocessor also calculates a bubble factor that represents the rate of formation and absorption of bubbles within tissue to determine minimum tissue impedance and maximum tissue conductance. The system further includes an electrosurgical instrument which includes one or more active electrodes adapted to apply electrosurgical energy to tissue.

15 Claims, 3 Drawing Sheets

U.S. PATENT DOCUMENTS

| | | | |
|---|---|---|---|
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,067,953 A | 11/1991 | Feucht |
| 5,075,839 A | 12/1991 | Fisher et al. |
| 5,087,257 A | 2/1992 | Farin |
| 5,099,840 A | 3/1992 | Goble et al. |

| Patent | Date | Inventor |
|---|---|---|
| 5,103,804 A | 4/1992 | Abele et al. |
| 5,108,389 A | 4/1992 | Cosmescu |
| 5,108,391 A | 4/1992 | Flachenecker |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,234,427 A | 8/1993 | Ohtomo et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson |
| 5,433,739 A | 7/1995 | Sluijter et al. |
| 5,436,566 A | 7/1995 | Thompson |
| 5,438,302 A | 8/1995 | Goble |
| 5,443,463 A | 8/1995 | Stern et al. |
| 5,445,635 A | 8/1995 | Denen |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,496,312 A | 3/1996 | Klicek |
| 5,496,313 A | 3/1996 | Gentelia et al. |
| 5,496,314 A | 3/1996 | Eggers |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa |
| 5,540,684 A | 7/1996 | Hassler, Jr. |
| 5,541,376 A | 7/1996 | Ladtkow et al. |
| 5,545,161 A | 8/1996 | Imran |
| 5,556,396 A | 9/1996 | Cohen et al. |
| 5,558,671 A | 9/1996 | Yates |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Bioarski et al. |
| 5,693,078 A | 12/1997 | Desai et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |

| | | | | | |
|---|---|---|---|---|---|
| 5,743,903 A | 4/1998 | Stern et al. | 6,074,089 A | 6/2000 | Hollander et al. |
| 5,749,869 A | 5/1998 | Lindenmeier et al. | 6,074,386 A | 6/2000 | Goble et al. |
| 5,749,871 A | 5/1998 | Hood et al. | 6,074,388 A | 6/2000 | Tockweiler et al. |
| 5,755,715 A | 5/1998 | Stern | 6,080,149 A | 6/2000 | Huang et al. |
| 5,766,153 A | 6/1998 | Eggers et al. | 6,088,614 A | 7/2000 | Swanson |
| 5,766,165 A | 6/1998 | Gentelia et al. | 6,093,186 A | 7/2000 | Goble |
| 5,769,847 A | 6/1998 | Panescu | 6,102,497 A | 8/2000 | Ehr et al. |
| 5,772,659 A | 6/1998 | Becker et al. | 6,102,907 A | 8/2000 | Smethers et al. |
| 5,788,688 A | 8/1998 | Bauer et al. | 6,113,591 A | 9/2000 | Whayne et al. |
| 5,792,138 A | 8/1998 | Shipp | 6,113,592 A | 9/2000 | Taylor |
| 5,797,902 A | 8/1998 | Netherly | 6,113,593 A | 9/2000 | Tu et al. |
| 5,807,253 A | 9/1998 | Dumoulin et al. | 6,113,596 A | 9/2000 | Hooven |
| 5,810,804 A | 9/1998 | Gough et al. | 6,123,701 A | 9/2000 | Nezhat |
| 5,814,092 A | 9/1998 | King | 6,123,702 A | 9/2000 | Swanson et al. |
| 5,817,091 A | 10/1998 | Nardella et al. | 6,132,429 A | 10/2000 | Baker |
| 5,817,093 A | 10/1998 | Williamson, IV et al. | 6,142,992 A | 11/2000 | Cheng et al. |
| 5,820,568 A | 10/1998 | Willis | 6,155,975 A | 12/2000 | Urich et al. |
| 5,827,271 A | 10/1998 | Bussey et al. | 6,162,184 A | 12/2000 | Swanson et al. |
| 5,830,212 A | 11/1998 | Cartmell | 6,162,217 A | 12/2000 | Kannenberg et al. |
| 5,836,909 A | 11/1998 | Cosmescu | 6,165,169 A | 12/2000 | Panescu et al. |
| 5,836,943 A | 11/1998 | Miller, III | 6,171,304 B1 | 1/2001 | Netherly et al. |
| 5,836,990 A | 11/1998 | Li | 6,183,468 B1 | 2/2001 | Swanson et al. |
| 5,843,019 A | 12/1998 | Eggers et al. | 6,186,147 B1 | 2/2001 | Cobb |
| 5,843,075 A | 12/1998 | Taylor | 6,188,211 B1 | 2/2001 | Rincon-Mora et al. |
| 5,846,236 A | 12/1998 | Lindenmeier et al. | 6,193,713 B1 | 2/2001 | Geistert et al. |
| 5,849,010 A | 12/1998 | Wurzer et al. | 6,197,023 B1 | 3/2001 | Muntermann |
| 5,853,409 A | 12/1998 | Swanson et al. | 6,203,541 B1 | 3/2001 | Keppel |
| 5,860,832 A | 1/1999 | Wayt et al. | 6,210,403 B1 | 4/2001 | Klicek |
| 5,865,788 A | 2/1999 | Edwards et al. | 6,216,704 B1 | 4/2001 | Ingle et al. |
| 5,868,737 A | 2/1999 | Taylor et al. | 6,222,356 B1 | 4/2001 | Taghizadeh-Kaschani |
| 5,868,739 A | 2/1999 | Lindenmeier et al. | 6,228,078 B1 | 5/2001 | Eggers et al. |
| 5,868,740 A | 2/1999 | LeVeen et al. | 6,228,080 B1 | 5/2001 | Gines |
| 5,871,481 A | 2/1999 | Kannenberg et al. | 6,228,081 B1 | 5/2001 | Goble |
| 5,891,142 A | 4/1999 | Eggers et al. | 6,231,569 B1 | 5/2001 | Bek |
| 5,897,552 A | 4/1999 | Edwards et al. | 6,232,556 B1 | 5/2001 | Daugherty et al. |
| 5,906,614 A | 5/1999 | Stern et al. | 6,235,020 B1 | 5/2001 | Cheng et al. |
| 5,908,444 A | 6/1999 | Azure | 6,235,022 B1 | 5/2001 | Hallock et al. |
| 5,913,882 A | 6/1999 | King | 6,237,604 B1 | 5/2001 | Burnside et al. |
| 5,921,982 A | 7/1999 | Lesh et al. | 6,238,387 B1 | 5/2001 | Miller, III |
| 5,925,070 A | 7/1999 | King et al. | 6,238,388 B1 | 5/2001 | Ellman |
| 5,931,836 A | 8/1999 | Hatta et al. | 6,241,723 B1 | 6/2001 | Heim et al. |
| 5,938,690 A | 8/1999 | Law et al. | 6,241,725 B1 | 6/2001 | Cosman |
| 5,944,553 A | 8/1999 | Yasui et al. | 6,243,654 B1 | 6/2001 | Johnson et al. |
| 5,948,007 A | 9/1999 | Starkebaum et al. | 6,245,061 B1 | 6/2001 | Panescu et al. |
| 5,951,545 A | 9/1999 | Schilling | 6,245,063 B1 | 6/2001 | Uphoff |
| 5,951,546 A | 9/1999 | Lorentzen | 6,245,065 B1 | 6/2001 | Panescu |
| 5,954,686 A | 9/1999 | Garito et al. | 6,246,912 B1 | 6/2001 | Sluijter et al. |
| 5,954,717 A | 9/1999 | Behl et al. | 6,251,106 B1 | 6/2001 | Becker et al. |
| 5,954,719 A | 9/1999 | Chen et al. | 6,254,422 B1 | 7/2001 | Feye-Hohmann |
| 5,957,961 A | 9/1999 | Maguire et al. | 6,258,085 B1 | 7/2001 | Eggleston |
| 5,959,253 A | 9/1999 | Shinchi | 6,261,285 B1 | 7/2001 | Novak |
| 5,961,344 A | 10/1999 | Rosales et al. | 6,261,286 B1 | 7/2001 | Goble et al. |
| 5,964,746 A | 10/1999 | McCary | 6,267,760 B1 | 7/2001 | Swanson |
| 5,971,980 A | 10/1999 | Sherman | 6,273,886 B1 | 8/2001 | Edwards |
| 5,971,981 A | 10/1999 | Hill et al. | 6,275,786 B1 | 8/2001 | Daners |
| 5,976,128 A | 11/1999 | Schilling et al. | 6,293,941 B1 | 9/2001 | Strul |
| 5,983,141 A | 11/1999 | Sluijter et al. | 6,293,942 B1 | 9/2001 | Goble et al. |
| 6,007,532 A | 12/1999 | Netherly | 6,293,943 B1 | 9/2001 | Panescu et al. |
| 6,010,499 A | 1/2000 | Cobb | 6,296,636 B1 | 10/2001 | Cheng et al. |
| 6,013,074 A | 1/2000 | Taylor | 6,306,131 B1 | 10/2001 | Hareyama et al. |
| 6,014,581 A | 1/2000 | Whayne et al. | 6,306,134 B1 | 10/2001 | Goble et al. |
| 6,017,338 A | 1/2000 | Brucker et al. | 6,309,386 B1 | 10/2001 | Bek |
| 6,022,346 A | 2/2000 | Panescu et al. | 6,322,558 B1 | 11/2001 | Taylor et al. |
| 6,022,347 A | 2/2000 | Lindenmeier et al. | 6,325,799 B1 | 12/2001 | Goble |
| 6,033,399 A | 3/2000 | Gines | 6,337,998 B1 | 1/2002 | Behl et al. |
| 6,039,731 A | 3/2000 | Taylor et al. | 6,338,657 B1 | 1/2002 | Harper et al. |
| 6,039,732 A | 3/2000 | Ichikawa et al. | 6,350,262 B1 | 2/2002 | Ashley |
| 6,041,260 A | 3/2000 | Stern et al. | 6,358,245 B1 | 3/2002 | Edwards |
| 6,044,283 A | 3/2000 | Fein et al. | 6,364,877 B1 | 4/2002 | Goble et al. |
| 6,053,910 A | 4/2000 | Fleenor | 6,371,963 B1 | 4/2002 | Nishtala et al. |
| 6,053,912 A | 4/2000 | Panescu et al. | 6,383,183 B1 | 5/2002 | Sekino et al. |
| 6,055,458 A | 4/2000 | Cochran et al. | 6,391,024 B1 | 5/2002 | Sun et al. |
| 6,056,745 A | 5/2000 | Panescu et al. | 6,398,779 B1 | 6/2002 | Buysse et al. |
| 6,056,746 A | 5/2000 | Goble et al. | 6,398,781 B1 | 6/2002 | Goble et al. |
| 6,059,781 A | 5/2000 | Yamanashi et al. | 6,402,741 B1 | 6/2002 | Keppel et al. |
| 6,063,075 A | 5/2000 | Mihori | 6,402,742 B1 | 6/2002 | Blewett et al. |
| 6,063,078 A | 5/2000 | Wittkampf | 6,402,743 B1 | 6/2002 | Orszulak et al. |
| 6,066,137 A | 5/2000 | Greep | 6,402,748 B1 | 6/2002 | Schoenman et al. |
| 6,068,627 A | 5/2000 | Orszulak et al. | 6,409,722 B1 | 6/2002 | Hoey et al. |

| | | |
|---|---|---|
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,087,054 B2 * | 8/2006 | Truckai et al. .................. 606/51 |
| 7,094,231 B1 | 8/2006 | Ellman et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |

| | | | |
|---|---|---|---|
| 7,146,210 B2 | 12/2006 | Palti | |
| 7,147,638 B2 | 12/2006 | Chapman et al. | |
| 7,151,964 B2 | 12/2006 | Desai et al. | |
| 7,153,300 B2 | 12/2006 | Goble | |
| 7,156,844 B2 | 1/2007 | Reschke et al. | |
| 7,156,846 B2 | 1/2007 | Dycus et al. | |
| 7,160,293 B2 | 1/2007 | Sturm et al. | |
| 7,163,536 B2 | 1/2007 | Godara | |
| 7,169,144 B2 | 1/2007 | Hoey et al. | |
| 7,172,591 B2 | 2/2007 | Harano et al. | |
| 7,175,618 B2 | 2/2007 | Dabney et al. | |
| 7,175,621 B2 | 2/2007 | Heim et al. | |
| 7,192,427 B2 | 3/2007 | Chapelon et al. | |
| 7,195,627 B2 | 3/2007 | Amoah et al. | |
| 7,203,556 B2 | 4/2007 | Daners | |
| 7,211,081 B2 | 5/2007 | Goble | |
| 7,214,224 B2 | 5/2007 | Goble | |
| 7,217,269 B2 | 5/2007 | El-Galley et al. | |
| 7,220,260 B2 | 5/2007 | Fleming et al. | |
| 7,223,264 B2 | 5/2007 | Daniel et al. | |
| 7,226,447 B2 | 6/2007 | Uchida et al. | |
| 7,229,469 B1 | 6/2007 | Witzel et al. | |
| 7,232,437 B2 | 6/2007 | Berman et al. | |
| 7,238,181 B2 | 7/2007 | Daners et al. | |
| 7,238,183 B2 | 7/2007 | Kreindel | |
| 7,244,255 B2 | 7/2007 | Daners et al. | |
| 7,247,155 B2 | 7/2007 | Hoey et al. | |
| 7,250,048 B2 | 7/2007 | Francischelli et al. | |
| 7,250,746 B2 | 7/2007 | Oswald et al. | |
| 7,255,694 B2 | 8/2007 | Keppel | |
| 7,258,688 B1 | 8/2007 | Shah et al. | |
| 7,282,048 B2 | 10/2007 | Goble et al. | |
| 7,282,049 B2 | 10/2007 | Orszulak et al. | |
| 7,285,117 B2 | 10/2007 | Krueger et al. | |
| 7,294,127 B2 | 11/2007 | Leung et al. | |
| 7,300,435 B2 | 11/2007 | Wham et al. | |
| 7,300,437 B2 | 11/2007 | Pozzato | |
| 7,303,557 B2 | 12/2007 | Wham et al. | |
| 7,305,311 B2 | 12/2007 | Van Zyl | |
| 7,317,954 B2 | 1/2008 | McGreevy | |
| 7,317,955 B2 | 1/2008 | McGreevy | |
| 7,324,357 B2 | 1/2008 | Miura et al. | |
| 7,333,859 B2 | 2/2008 | Rinaldi et al. | |
| 7,341,586 B2 | 3/2008 | Daniel et al. | |
| 7,344,532 B2 | 3/2008 | Goble et al. | |
| 7,353,068 B2 | 4/2008 | Tanaka et al. | |
| 7,354,436 B2 | 4/2008 | Rioux et al. | |
| 7,357,800 B2 | 4/2008 | Swanson | |
| 7,364,577 B2 | 4/2008 | Wham et al. | |
| 7,364,578 B2 | 4/2008 | Francischelli et al. | |
| 7,364,972 B2 | 4/2008 | Ono et al. | |
| 7,367,972 B2 | 5/2008 | Francischelli et al. | |
| RE40,388 E | 6/2008 | Gines | |
| 7,396,336 B2 | 7/2008 | Orszulak et al. | |
| 7,402,754 B2 | 7/2008 | Kirwan, Jr. et al. | |
| D574,323 S | 8/2008 | Waaler | |
| 7,407,502 B2 | 8/2008 | Strul et al. | |
| 7,416,437 B2 | 8/2008 | Sartor et al. | |
| 7,416,549 B2 | 8/2008 | Young et al. | |
| 7,422,582 B2 | 9/2008 | Malackowski et al. | |
| 7,422,586 B2 | 9/2008 | Morris et al. | |
| 7,425,835 B2 | 9/2008 | Eisele | |
| 7,465,302 B2 | 12/2008 | Odell et al. | |
| 7,470,272 B2 | 12/2008 | Mulier et al. | |
| 7,479,140 B2 | 1/2009 | Ellman et al. | |
| 7,491,199 B2 | 2/2009 | Goble | |
| 7,491,201 B2 | 2/2009 | Shields et al. | |
| 7,513,896 B2 | 4/2009 | Orszulak | |
| 7,525,398 B2 | 4/2009 | Nishimura et al. | |
| 7,736,358 B2 | 6/2010 | Shores | |
| 2002/0052599 A1 | 5/2002 | Goble | |
| 2003/0181898 A1 | 9/2003 | Bowers | |
| 2003/0199863 A1 | 10/2003 | Swanson | |
| 2004/0015159 A1 | 1/2004 | Slater et al. | |
| 2004/0015163 A1* | 1/2004 | Buysse et al. | 606/34 |
| 2004/0030330 A1 | 2/2004 | Brassell et al. | |
| 2004/0068304 A1 | 4/2004 | Paton | |
| 2004/0097912 A1 | 5/2004 | Gonnering | |
| 2004/0143263 A1 | 7/2004 | Schechter et al. | |
| 2004/0172016 A1 | 9/2004 | Bek et al. | |
| 2005/0004564 A1 | 1/2005 | Wham | |
| 2005/0004567 A1* | 1/2005 | Daniel et al. | 606/50 |
| 2005/0004634 A1 | 1/2005 | Ricart et al. | |
| 2005/0021020 A1 | 1/2005 | Blaha et al. | |
| 2005/0109111 A1 | 5/2005 | Manlove et al. | |
| 2005/0182398 A1 | 8/2005 | Paterson | |
| 2005/0197659 A1 | 9/2005 | Bahney | |
| 2005/0203504 A1 | 9/2005 | Wham et al. | |
| 2006/0025760 A1 | 2/2006 | Podhajsky | |
| 2006/0079871 A1 | 4/2006 | Plaven et al. | |
| 2006/0111711 A1 | 5/2006 | Goble | |
| 2006/0161148 A1 | 7/2006 | Behnke | |
| 2006/0178664 A1 | 8/2006 | Keppel | |
| 2006/0224152 A1 | 10/2006 | Behnke et al. | |
| 2006/0281360 A1 | 12/2006 | Sartor et al. | |
| 2006/0291178 A1 | 12/2006 | Shih | |
| 2007/0038209 A1 | 2/2007 | Buysse et al. | |
| 2007/0093800 A1 | 4/2007 | Wham et al. | |
| 2007/0093801 A1 | 4/2007 | Behnke | |
| 2007/0135812 A1 | 6/2007 | Sartor | |
| 2007/0173802 A1 | 7/2007 | Keppel | |
| 2007/0173803 A1 | 7/2007 | Wham et al. | |
| 2007/0173804 A1 | 7/2007 | Wham et al. | |
| 2007/0173805 A1 | 7/2007 | Weinberg et al. | |
| 2007/0173806 A1 | 7/2007 | Orszulak et al. | |
| 2007/0173810 A1 | 7/2007 | Orszulak | |
| 2007/0173813 A1 | 7/2007 | Odom | |
| 2007/0208339 A1 | 9/2007 | Arts et al. | |
| 2007/0225698 A1 | 9/2007 | Orszulak et al. | |
| 2007/0250052 A1 | 10/2007 | Wham | |
| 2007/0265612 A1 | 11/2007 | Behnke et al. | |
| 2007/0282320 A1 | 12/2007 | Buysse et al. | |
| 2008/0015563 A1 | 1/2008 | Hoey et al. | |
| 2008/0015564 A1 | 1/2008 | Wham et al. | |
| 2008/0039831 A1 | 2/2008 | Odom et al. | |
| 2008/0039836 A1 | 2/2008 | Odom et al. | |
| 2008/0082094 A1 | 4/2008 | McPherson et al. | |
| 2008/0125767 A1 | 5/2008 | Blaha | |
| 2008/0177199 A1 | 7/2008 | Podhajsky | |
| 2008/0248685 A1 | 10/2008 | Sartor et al. | |
| 2008/0281315 A1 | 11/2008 | Gines | |
| 2008/0281316 A1 | 11/2008 | Carlton et al. | |
| 2008/0287791 A1 | 11/2008 | Orszulak et al. | |
| 2008/0287838 A1 | 11/2008 | Orszulak et al. | |
| 2009/0018536 A1 | 1/2009 | Behnke | |
| 2009/0024120 A1 | 1/2009 | Sartor | |
| 2009/0036883 A1 | 2/2009 | Behnke | |
| 2009/0069801 A1 | 3/2009 | Jensen et al. | |
| 2009/0082765 A1 | 3/2009 | Collins et al. | |
| 2009/0157071 A1 | 6/2009 | Wham et al. | |
| 2009/0157072 A1 | 6/2009 | Wham et al. | |
| 2009/0157073 A1 | 6/2009 | Orszulak | |
| 2009/0157075 A1 | 6/2009 | Wham et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |

| | | |
|---|---|---|
| DE | 19717411 | 11/1998 |
| DE | 19848540 | 2/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1707144 | 3/2006 |
| EP | 1645235 | 4/2006 |
| EP | 880220 | 6/2006 |
| EP | 1707143 | 10/2006 |
| EP | 1744354 | 1/2007 |
| EP | 1810628 | 7/2007 |
| EP | 1810630 | 7/2007 |
| EP | 1810633 | 7/2007 |
| EP | 1854423 | 11/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO95/25471 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO02/00129 | 1/2002 |
| WO | WO02/11634 | 2/2002 |
| WO | WO 02/32335 | 4/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/043240 | 5/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060365 | 7/2005 |
| WO | WO2005/060849 | 7/2005 |
| WO | WO2006/050888 | 5/2006 |
| WO | WO2006/105121 | 10/2006 |
| WO | WO 2008/003058 | 1/2008 |

OTHER PUBLICATIONS

International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation—'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.

Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Muller et al. "Extended Left Hemicolectomy Using the LigaSure Vessel Sealing System" Innovations That Work; Sep. 1999.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 05002769.7 dated Jun. 9, 2006.
International Search Report EP 06000708.5 dated Apr. 21, 2006.
International Search Repor—extended EP 06000708.5 dated Aug. 22, 2006.
International Search Report EP 06006717.0 dated Aug. 7, 2006.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001527.6 dated May 9, 2007.
International Search Report EP 07004355.9 dated May 21, 2007.
International Search Report EP 07008207.8 dated Sep. 5, 2007.
International Search Report EP 07010673.7 dated Sep. 24, 2007.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report No. PCT/US2009/046870 dated Jul. 21, 2009.
Supp. EP Search Report dated Nov. 29, 2011 for EP 09 76 3515.
US 6,878,148, 04/2005, Goble et al. (withdrawn)

* cited by examiner

SYSTEM AND METHOD FOR OUTPUT CONTROL OF ELECTROSURGICAL GENERATOR

BACKGROUND

1. Technical Field

The present disclosure relates to a system and method for performing electrosurgical procedures. More particularly, the present disclosure relates to a system and method for controlling output of an electrosurgical generator based on sensed tissue feedback.

2. Background of Related Art

Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

Ablation is a monopolar procedure which is particularly useful in the field of neurosurgery and cancer tumor hyperthermia, where one or more RF ablation needle electrodes (usually of elongated cylindrical geometry) are inserted into a living body. A typical form of such needle electrodes incorporates an insulated sheath from which an exposed (uninsulated) tip extends. When RF energy is provided between the return electrode and the inserted ablation electrode, RF current flows from the needle electrode through the body. Typically, the current density is very high near the tip of the needle electrode, which tends to heat and destroy surrounding tissue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

It is known in the art that sensed tissue feedback may be used to control delivery of electrosurgical energy. Therefore, a need exists to develop an electrosurgical system and method which allows for precisely controlling output of an electrosurgical generator based on sensed tissue feedback.

SUMMARY

The present disclosure relates to a system and method for performing electrosurgical procedures. The system continuously monitors impedance during an electrosurgical procedure as energy is being applied to the tissue. The system generates a variance impedance curve based on the measured impedance and a moving time window which represents a segment of the variance impedance curve. The system calculates a slope of the segment to determine if the slope is within a predetermined threshold. Once the predetermined slope threshold is reached, the system calculates a bubble factor that represents the rate of formation and absorption of bubbles within tissue. Depending on the calculated bubble factor, the system adjusts the power output to maintain the bubble factor within a predetermined bubble factor threshold. This ensures that the impedance of the tissue is maintained at a minimum thereby providing maximum conductance.

According to one aspect of the present disclosure a system is provided. The system includes an electrosurgical generator adapted to supply electrosurgical energy to tissue. The generator includes sensor circuitry adapted to continuously monitor tissue impedance to generate a variance impedance curve and a microprocessor adapted to calculate a slope of a segment of the variance impedance curve. The microprocessor also calculates a bubble factor that represents the rate of formation and absorption of bubbles within tissue to determine minimum tissue impedance and maximum tissue conductance. The system further includes an electrosurgical instrument which includes one or more active electrodes adapted to apply electrosurgical energy to tissue.

According to another aspect of the present disclosure a method for performing electrosurgical procedures is provided. The method includes the steps of applying electrosurgical energy to tissue from an electrosurgical generator and continuously monitoring tissue impedance to generate a variance impedance curve. The method further includes the steps of calculating a slope of a segment of the variance impedance curve and calculating a bubble factor representing rate of formation and absorption of bubbles within tissue to determine minimum tissue impedance and maximum tissue conductance.

According to a further aspect of the present disclosure an electrosurgical generator adapted to supply electrosurgical energy to tissue is provided. The generator includes sensor circuitry adapted to continuously monitor tissue impedance to generate a variance impedance curve and a microprocessor adapted to calculate a slope of a segment of the variance impedance curve and bubble factor representing rate of formation and absorption of bubbles within tissue to determine minimum tissue impedance and maximum tissue conductance.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical systems.

Figure 1:
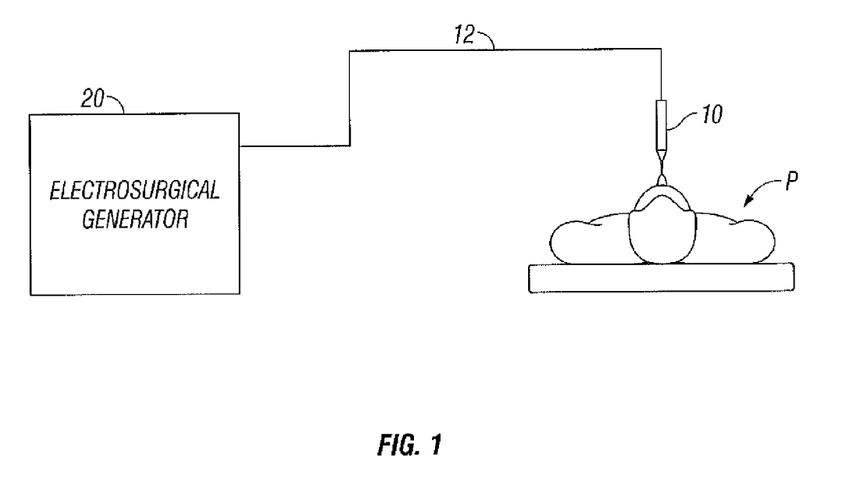
FIG. 1 is a schematic block diagram of an electrosurgical system according to the present disclosure.

FIG. 1 is a schematic illustration of an electrosurgical system according to the present disclosure. The system includes an electrosurgical instrument 10 having one or more electrodes for treating tissue of a patient P. The instrument 10 may be either of monopolar type including one or more active electrodes (e.g., electrosurgical cutting probe, ablation electrodes), etc.) or of bipolar type including one or more active and return electrodes (e.g., electrosurgical sealing forceps). Electrosurgical RF energy is supplied to the instrument 10 by a generator 20 via a supply line 12, which is operably connected to an active output terminal, allowing the instrument 10 to coagulate, seal, ablate and/or otherwise treat tissue.

If the instrument 10 is of monopolar type then energy may be returned to the generator 20 through a return electrode (not explicitly shown) which may be one or more electrode pads disposed on the patient's body. The system may include a plurality of return electrodes which are believed to minimize the chances of damaged tissue by maximizing the overall contact area with the patient P. In addition, the generator 20 and the monopolar return electrode may be configured for monitoring so called "tissue-to-patient" contact to insure that sufficient contact exists therebetween to further minimize chances of tissue damage.

If the instrument 10 is of bipolar type, the return electrode is disposed in proximity to the active electrode (e.g., on opposing jaws of bipolar forceps). It is also envisioned that the generator 20 may include a plurality of supply and return terminals and a corresponding number of electrode leads.

The generator 20 includes input controls (e.g., buttons, activators, switches, touch screen, etc.) for controlling the generator 20. In addition, the generator 20 may include one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task (e.g., coagulating, tissue sealing, intensity setting, etc.). It is also envisioned that the instrument 10 may include a plurality of input controls which may be redundant with certain input controls of the generator 20. Placing the input controls at the instrument 10 allows for easier and faster modification of RF energy parameters during the surgical procedure without requiring interaction with the generator 20.

Figure 2:
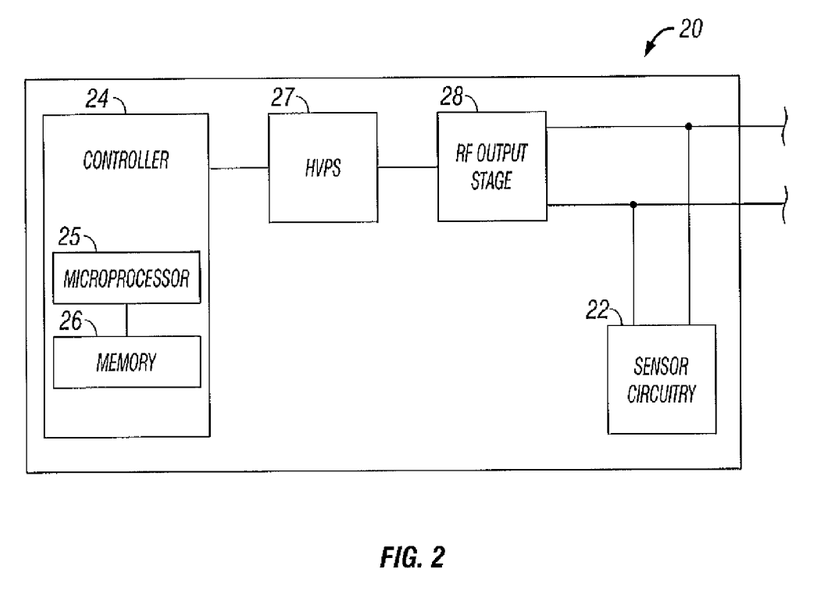
FIG. 2 is a schematic block diagram of a generator according to the present disclosure.

FIG. 2 shows a schematic block diagram of the generator 20 having a controller 24, a high voltage DC power supply 27 ("HVPS") and an RF output stage 28. The HVPS 27 provides high voltage DC power to an RF output stage 28 which then converts high voltage DC power into RF energy and delivers the RF energy to the active electrode of the instrument 10. In particular, the RF output stage 28 generates sinusoidal waveforms of high frequency RF energy. The RF output stage 28 is configured to generate a plurality of waveforms having various duty cycles, peak voltages, crest factors, and other parameters. Certain types of waveforms are suitable for specific electrosurgical modes. For instance, the RF output stage 28 generates a 100% duty cycle sinusoidal waveform in cut mode, which is best suited for dissecting tissue and a 25% duty cycle waveform in coagulation mode, which is best used for cauterizing tissue to stop bleeding.

The controller 24 includes a microprocessor 25 operably connected to a memory 26 which may be volatile type memory (e.g., RAM) and/or non-volatile type memory (e.g., flash media, disk media, etc.). The microprocessor 25 includes an output port which is operably connected to the HVPS 27 and/or RF output stage 28 allowing the microprocessor 25 to control the output of the generator 20 according to either open and/or closed control loop schemes.

A closed loop control scheme is a feedback control loop wherein sensor circuitry 22, which may include a plurality of sensors measuring a variety of tissue and energy properties (e.g., tissue impedance, tissue temperature, output current and/or voltage, etc.), provides feedback to the controller 24. Such sensors are within the purview of those skilled in the art. The controller 24 then signals the HVPS 27 and/or RA output stage 28 which then adjust DC and/or RF power supply, respectively. The controller 24 also receives input signals from the input controls of the generator 20 or the instrument 10. The controller 24 utilizes the input signals to adjust power outputted by the generator 20 and/or performs other control functions thereon.

Figure 3:
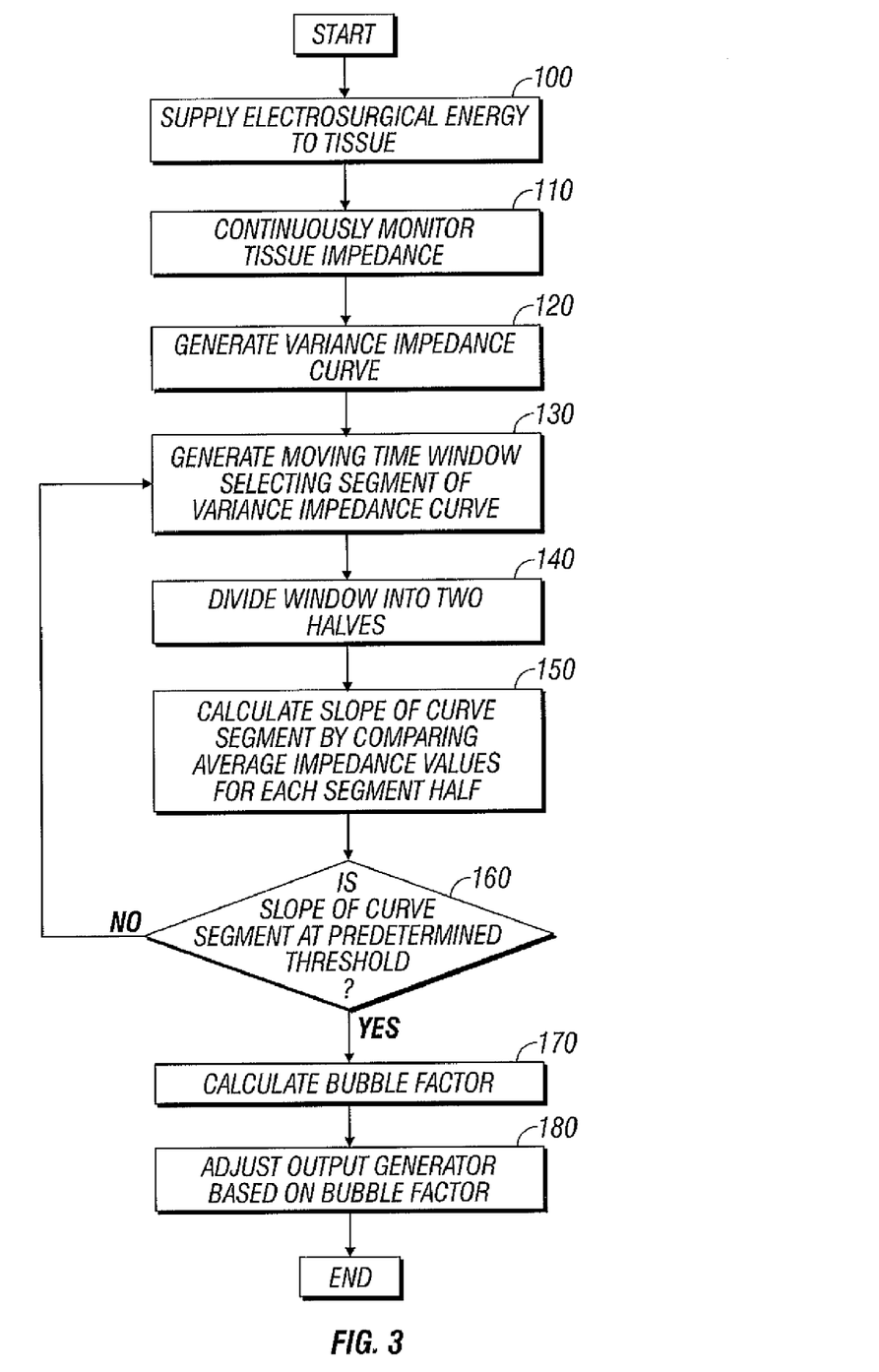
FIG. 3 is a flow diagram illustrating a method according to the present disclosure.

FIG. 3 shows a method according to the present disclosure for controlling output of the generator in response to monitored tissue impedance. In step 100, the instrument 10 is brought into a treatment site of the tissue and the generator 20 supplies electrosurgical energy to the tissue through the instrument 10. In step 110, during application of energy to the tissue, impedance is continuously monitored by the sensor circuitry 22. In particular, voltage and current signals are monitored and corresponding impedance values are calculated at the sensor circuitry 22 and/or at the microprocessor 25. Power and other energy properties may also be calculated based on collected voltage and current signals. The microprocessor 25 stores the collected voltage, current, and impedance within the memory 26.

Figure 4:
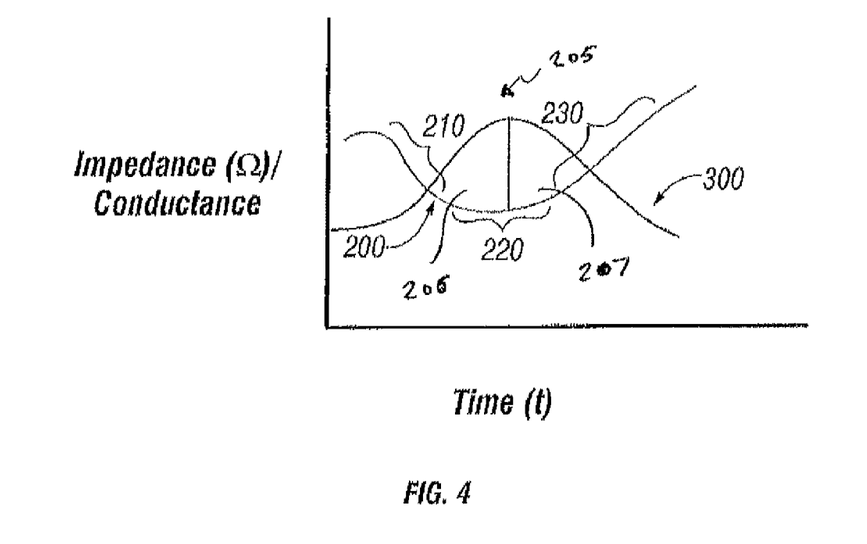
FIG. 4 is an illustrative graph showing average impedance values over time.
Figure 5:
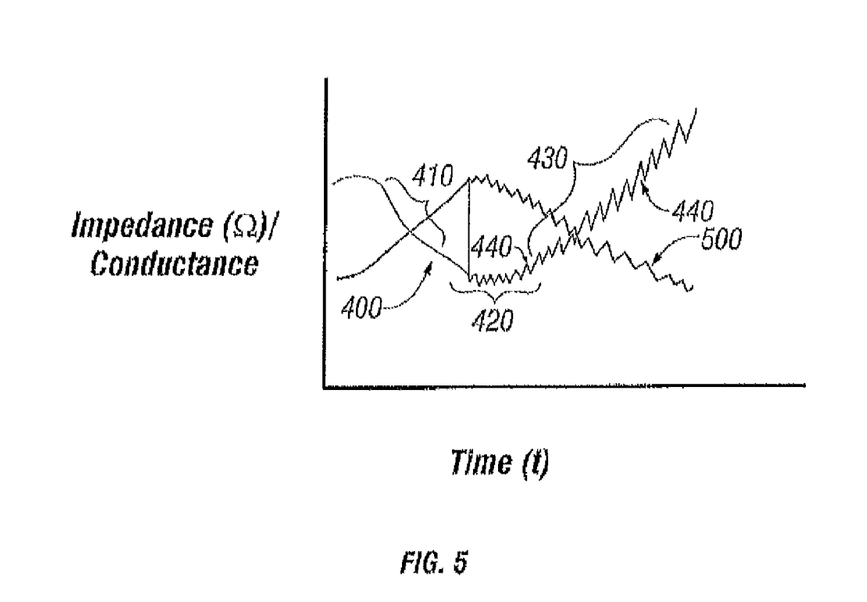
FIG. 5 is an illustrative graph showing variance impedance values over time according to the present disclosure.

Changes in impedance of tissue undergoing electrosurgical treatment (e.g., ablation) are illustrated in FIGS. 4 and 5, FIG. 4 shows an averaged impedance curve 200 which is generated based on time averaged RMS impedance values, thus, it appears smooth (i.e., lacking variation between the values). Initially, there is a slow drop 210 in impedance as energy is applied. After the tissue reacts, which occurs at a cusp 220, there is a quick rise 230. FIG. 4 also shows a conductance curve 300, which is an inverse of the impedance curve 200.

Impedance of tissue follows the general trend of the averaged impedance curve 200, however, the averaged impedance curve 200 lacks detail a of minute impedance variations. These variations are shown in a variance impedance curve 400 in FIG. 5. In step 120, the generator 20 plots the variance impedance curve 400 based on measured impedances values. In the variance impedance curve 400, the impedance values are not time-averaged and represent every change in impedance measured by the sensor circuitry 22. Initially, there is a slow drop 410 which is smooth, however, a cusp 420 and a rise 430 show significant variance 440. The variance 440 is indicative of rapid changes in impedance. When high frequency RF electrosurgical energy is applied to tissue, temperature at the site rises beyond 100° C. which occurs approximately at the cusp 420. At this temperature, water within the tissue is converted into steam thereby forming bubbles within tissue. Hence, as impedance rises during the rise 430, tissue is in a state of equilibrium between dehydration and hydration, as bubbles continually form and reabsorb. Rise in impedance is also associated with formation of bubbles around the exposed electrode of the instrument 10. Thus, the variance 440 is reflective of changes in moisture content of the tissue caused by bubble formation/reabsorption.

FIG. 5 also shows a conductance curve 500, which is inversely related to the impedance curve 400. Thus, cusps 220 and 420 represent the maximum point of conductance wherein a maximum amount energy can be supplied to the tissue. Hence, maintaining impedance at its minimum (e.g., cusps 220 and 420) maximizes conduction. Thus, it is desirable to supply energy from the generator 20 at such a level so that maximum conductance is continually maintained.

In steps 130-170, a point of maximum conductance which corresponds to the cusp 420, is determined by analyzing the slope and variance of the impedance. In particular, in step 130, as shown in FIGS. 4 and 5, a moving time window 205, which is synchronized with actual running time, is generated. The time window 205 is moved along the variance impedance curve 400 as the procedure progresses and selects a specific segment thereof for analysis. It is envisioned that the time period represented by the window 205 may be from about 2 to about 15 seconds. The window may be realized as a FIFO (e.g., first in first out) buffer which is within purview of those skilled in the art.

In step 140, the window 205 is divided into a first half 206 and a second half 207. In step 150, an average impedance value is determined for the halves of the window 205, namely the impedance values of the first and second halves 206 and 207 are averaged. The slope of the impedance curve 400 is calculated by comparing the average impedance values of the first and second halves 206 and 207. If the average of the second half 207 is less than the average of the first half 206 then the slope is negative (e.g., the curve is decreasing). If the average of the second half 207 is greater than the average of the first half 206 then the slope is positive (e.g., the curve is increasing). The relationship between the average impedance values of the first and second halves 206 and 207 and the slope may also be expressed by the formula (1):

$$\text{Average of second half} - \text{average of first half} = \text{slope}. \tag{1}$$

Determining the slope of the impedance curve locates an approximate point on the curve which corresponds to tissue impedance at which energy conductance into the tissue is most effective.

In step 160, the slope is compared with a predetermined slope threshold. It is envisioned the slope threshold may be approximately zero to represent the cusp 420 which coincides with maximum conductance.

The comparison step 160 allows for determining a point at which bubble formation begins to occur. Since bubble formation occurs only after the slow drop 410 at the cusp 420 "bubbling" does not occur until this point is reached. Hence, the method proceeds to step 170 only after the slope corresponds to a point on the impedance curve 400 at which bubbles begin forming thereby preventing unnecessary calculations of so called "bubble factors."

If the slope corresponds to the threshold slope representative of a point at which bubbles begin forming (e.g., the cusp 420), the method proceeds to step 170 where a bubble factor is calculated by subtracting variance of the first half 206 from the variance of the second half 207 as expressed by the formula (2):

$$\text{Variance of second half} - \text{variance of first half} = \text{bubble factor}. \tag{2}$$

Thus, the bubble factor is the difference between the variances of the impedance values. The bubble factor identifies the changes in bubble formation.

The real-time peak-to-peak variance which is used to calculate the bubble factor is more useful in determining the minimum impedance (i.e., maximum conductance) than the averaged RMS impedance signal since the peaks are more easily determined.

In step 180 power adjustments to the output of the generator 20 are made based on the bubble factor. If the calculated bubble factor is positive, the variance in the second half 207 is larger than the variance in the first half 206 which represents increased bubble formation. In response to a positive bubble factor, the generator 20 decreases power. If the bubble factor is negative, which means that the variance in the first half 206 is larger than the variance in the second half 207, i.e., rate of bubble formation is decreasing, the power output is increased.

If the bubble factor is approximately zero, which denotes that bubble formation is approximately being held constant, the power output is maintained at its current level. As a result, the output of the generator 20 is controlled as a function of the bubble factor. In particular, the output of the generator 20 is adjusted so that the slope of impedance and bubble factor are maintained at a predetermined threshold, wherein the bubble formation is kept at a predetermined level as expressed by the bubble factor threshold. This allows for maintaining maximum conductance of the tissue resulting in efficient energy being transferred to the tissue as well as increased accuracy and repeatability of hyperthermal treatments.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system comprising:
   an electrosurgical generator adapted to supply electrosurgical energy to tissue, the generator including:
   sensor circuitry adapted to continuously monitor tissue impedance to generate a variance impedance curve; and
   a microprocessor programmed to calculate a slope of at least one segment of the variance impedance curve and a bubble factor representing rate of formation and absorption of bubbles within tissue to determine minimum tissue impedance and maximum tissue conductance; and
   an electrosurgical instrument including at least one active electrode adapted to apply electrosurgical energy to tissue;
   wherein the microprocessor is further programmed to generate a moving time window to select the at least one segment of the variance impedance curve and divide the at least one segment into a first half and a second half, the first half representing a downward slope having a minimum impedance and the second half representing an upward slope advancing toward a maximum impedance.

2. A system according to claim 1, wherein the microprocessor is further adapted to adjust output of the electrosurgical generator as a function of the bubble factor to maintain minimum tissue impedance and maximum tissue conductance.

3. A system according to claim 1, wherein the microprocessor is further adapted to calculate a first average impedance value for the first half of the at least one segment and a second average impedance value for the second half of the at least one segment and compare the first and second average impedance values.

4. A system according to claim 1, wherein the microprocessor is further adapted to calculate a first variance of impedance values for the first half of the at least one segment and a second variance of impedance values for the second half of the at least one segment and subtract the first variance of impedance values from the second variance of impedance values.

5. A system according to claim 4, wherein the microprocessor is further adapted to adjust output of the electrosurgical generator as a function of the bubble factor, wherein if the calculated bubble factor is positive, output is decreased, if the bubble factor is negative, output is increased, and if the bubble factor is approximately zero, the output is unchanged.

6. A method for performing electrosurgical procedures:
applying electrosurgical energy to tissue from an electrosurgical generator;
continuously monitoring tissue impedance to generate a variance impedance curve;
calculating a slope of at least one segment of the variance impedance curve;
calculating a bubble factor representing rate of formation and absorption of bubbles within tissue to determine minimum tissue impedance and maximum tissue conductance;
generating a moving time window to select the at least one segment of the variance impedance curve; and
dividing the at least one segment into a first half and a second half the first half representing a downward slope having a minimum impedance and the second half representing an upward slope advancing toward a maximum impedance.

7. A method according to claim 6, further comprising the step of:
adjusting output of the electrosurgical generator as a function of the bubble factor to maintain minimum tissue impedance and maximum tissue conductance.

8. A method according to claim 6, wherein the step of calculating a slope comprises:
calculating a first average impedance value for the first half of the at least one segment and a second average impedance value for the second half of the at least one segment; and
comparing the first and second average impedance values.

9. A method according to claim 6, wherein the step of calculating a bubble factor comprises:
calculating a first variance of impedance values for the first half of the at least one segment and a second variance of impedance values for the second half of the at least one segment; and
subtracting the first variance of impedance values from the second variance of impedance values.

10. A method according to claim 9, further comprising the step of:
adjusting output of the electrosurgical generator as a function of the bubble factor, wherein if the calculated bubble factor is positive, output is decreased, if the bubble factor is negative, output is increased, and if the bubble factor is approximately zero, the output is unchanged.

11. An electrosurgical generator adapted to supply electrosurgical energy to tissue comprising:
sensor circuitry adapted to continuously monitor tissue impedance to generate a variance impedance curve; and
a microprocessor programmed to calculate a slope of at least one segment of the variance impedance curve and a bubble factor representing rate of formation and absorption of bubbles within tissue to determine minimum tissue impedance and maximum tissue conductance;
wherein the microprocessor is further programmed to generate a moving time window to select the at least one segment of the variance impedance curve and divide the at least one segment into a first half and a second half, the first half representing a downward slope having a minimum impedance and the second half representing an upward slope advancing toward a maximum impedance.

12. An electrosurgical generator according to claim 11, wherein the microprocessor is further adapted to adjust output of the electrosurgical generator as a function of the bubble factor to maintain minimum tissue impedance and maximum tissue conductance.

13. An electrosurgical generator according to claim 11, wherein the microprocessor is further adapted to calculate a first average impedance value for the first half of the at least one segment and a second average impedance value for the second half of the at least one segment and comparing the first and second average impedance values.

14. An electrosurgical generator according to claim 11, wherein the microprocessor is further adapted to calculate a first variance of impedance values for the first half of the at least one segment and a second variance of impedance values for the second half of the at least one segment and subtracting the first variance of impedance values from the second variance of impedance values.

15. An electro surgical generator according to claim 14, wherein the microprocessor is further adapted to adjust output of the electrosurgical generator as a function of the bubble factor, wherein if the calculated bubble factor is positive, output is decreased, if the bubble factor is negative, output is increased, and if the bubble factor is approximately zero, the output is unchanged.

* * * * *